US006999171B2

(12) United States Patent
Kusuzawa (10) Patent No.: US 6,999,171 B2
(45) Date of Patent: Feb. 14, 2006

(54) APPARATUS AND METHOD FOR MEASURING PARTICLE SIZE

(75) Inventor: Hideo Kusuzawa, Kobe (JP)

(73) Assignee: Sysmex Corporation, Kobe (JP)

(*) Notice: Subject to any disclaimer, the term of this patent is extended or adjusted under 35 U.S.C. 154(b) by 376 days.

(21) Appl. No.: 10/213,080

(22) Filed: Aug. 7, 2002

(65) Prior Publication Data

US 2003/0030803 A1  Feb. 13, 2003

(30) Foreign Application Priority Data

Aug. 7, 2001 (JP) .............................. 2001-239440

(51) Int. Cl.
G01N 15/02 (2006.01)
(52) U.S. Cl. ..................................... 356/336
(58) Field of Classification Search ................ 356/335, 356/336, 337, 338, 339, 340, 341, 342
See application file for complete search history.

(56) References Cited

U.S. PATENT DOCUMENTS

| 3,757,213 | A |   | 9/1973  | Coulter et al. |
| 5,619,043 | A | * | 4/1997  | Preikschat et al. ......... 250/574 |
| 5,784,160 | A | * | 7/1998  | Naqwi ....................... 356/496 |
| 5,815,264 | A | * | 9/1998  | Reed et al. ................. 356/336 |
| 5,825,477 | A | * | 10/1998 | Furuie ......................... 356/72 |
| 5,861,950 | A |   | 1/1999  | Knowlton |
| 6,180,415 | B1 | * | 1/2001  | Schultz et al. .............. 436/518 |
| 6,219,476 | B1 | * | 4/2001  | Kususawa et al. ............ 385/33 |
| 6,423,956 | B1 | * | 7/2002  | Mandella et al. ......... 250/201.3 |
| 6,423,958 | B1 | * | 7/2002  | Okamoto et al. ......... 250/208.1 |

FOREIGN PATENT DOCUMENTS

| JP | 08-136439    |   | 5/1996  |
| JP | 2000-131616 A |   | 5/2000  |
| JP | 2000-186999 A |   | 7/2000  |
| JP | 2000131616   | * | 12/2000 |
| JP | 2002-71549 A |   | 3/2002  |

OTHER PUBLICATIONS

Black, D.L. et al., Laser-Based Techniques for Particle-Size Measurement: A Review of Sizing Methods and Their Industrial Applications, Progress in Energy and Combustion Science, Elsevier Science Publishers, Amsterdam, NL, vol. 22, No. 3, 1996, pp. 267-306.

* cited by examiner

*Primary Examiner*—Gregory J. Toatley, Jr.
*Assistant Examiner*—Roy M. Punnoose
(74) *Attorney, Agent, or Firm*—Birch, Stewart, Kolasch & Birch, LLP (57) ABSTRACT

A particle size measuring apparatus includes a laser light source; a coherence reducing element for receiving laser light emitted by the laser light source, reducing coherence of the laser light and emitting the laser light whose coherence is reduced; a ring light forming section for converting the light emitted by the coherence reducing element into ring light; an internal reflection mirror for concentrating the ring light on a particle to be measured and illuminating the particle; an object lens for receiving scattered light from the illuminated particle inside the ring light; a photoreceptive element for receiving the scattered light through the object lens; and a calculating section for calculating a size of the particle from the intensity of the scattered light obtained by the photoreceptive element by using a monotone increasing function.

6 Claims, 8 Drawing Sheets

APPARATUS AND METHOD FOR MEASURING PARTICLE SIZE

CROSS-REFERENCE TO RELATED APPLICATION

This application is related to Japanese Patent Application No. 2001-239440 filed on Aug. 7, 2001 whose priority is claimed under 35 USC § 119, the disclosure of which is incorporated by reference in its entirety.

BACKGROUND OF THE INVENTION

1. Field of the Invention

The present invention relates to an apparatus for measuring a particle size and a method for measuring the particle size.

2. Description of the Related Art

As conventional methods for measuring the particle size, there are known an electric detection method of electrically detecting a volume of the particle which is suspended in an electrolytic solution (see U.S. Pat. No. 3,757,213, for example) and an image analysis method of optically capturing an image of the particle and analyzing the size of the particle from the captured image (see Japanese Unexamined Patent Publication No. HEI 8(1996)-136439, for example).

As another method of measuring the particle size, there is known a method of estimating the particle size from light scattering characteristics of the particle. However, it is not easy to find out a light scattering characteristic such as shows a good and simple correspondence to the particle size, and therefore, a problem lies in that complicated calculation is required for obtaining the particle size from the scattered light.

SUMMARY OF THE INVENTION

The inventor of the present invention has found a principle that the size of a particle can be easily measured by applying dark-field illumination to the particle with a laser beam with decreased coherence. An object of the present invention is to provide a particle size measuring apparatus and method capable of measuring the particle size efficiently by taking advantage of the principle.

The present invention provides a particle size measuring apparatus comprising a laser light source; a coherence reducing element for receiving laser light emitted by the laser light source, reducing coherence of the laser light and emitting the laser light whose coherence is reduced; a ring light forming section for converting the light emitted by the coherence reducing element into a ring light; an internal reflection mirror for concentrating the ring light on a particle to be measured and illuminating the particle; an object lens for receiving scattered light from the illuminated particle inside the ring light; a photoreceptive element for receiving the scattered light through the object lens; and a calculating section for calculating a size of the particle from an intensity of the scattered light obtained by the photoreceptive element by using a monotone increasing function.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 10($a$) to 10($c$) illustrate an illumination moire formed on a particle; and FIGS. 11($a$) to 11($c$) illustrate an illumination moire formed on a particle.

DESCRIPTION OF THE PREFERRED EMBODIMENTS

According to the present invention, the particle size measuring apparatus includes a laser light source; a coherence reducing element for receiving laser light emitted by the laser light source, reducing coherence of the laser light and emitting the laser light whose coherence is reduced; a ring light forming section for converting the light emitted by the coherence reducing element into a ring light; an internal reflection mirror for concentrating the ring light on a particle to be measured and illuminating the particle; an object lens for receiving scattered light from the illuminated particle inside the ring light; a photoreceptive element for receiving the scattered light through the object lens; and a calculating section for calculating a size of the particle from an intensity of the scattered light obtained by the photoreceptive element by using a monotone increasing function.

Particles to be measured by the apparatus of the present invention include substances contained in blood and urine, inorganic particles such as fine ceramics, pigments, cosmetic powder, toners and abrasive powder, and organic particle such as food additives. The particles are about 1 to 20 $\mu$m in size.

The particle to be measured by the apparatus may be floating in liquid or may be fixed on a plate such as a slide glass.

One feature of the present invention is dark-field illumination, that is, the ring light is concentrated from around the object lens to illuminate the particle to be measured and scattered light from the particle is received inside the ring light.

Another feature of the present invention is the use of the coherence reducing element for reducing the coherence of the laser light emitted from the laser light source.

Now explanation is given of the principle according to the present invenion for calculating the particle size from the intensity of the scattered light obtained by the photoreceptive element using a monotone increasing function.

Figure 8:
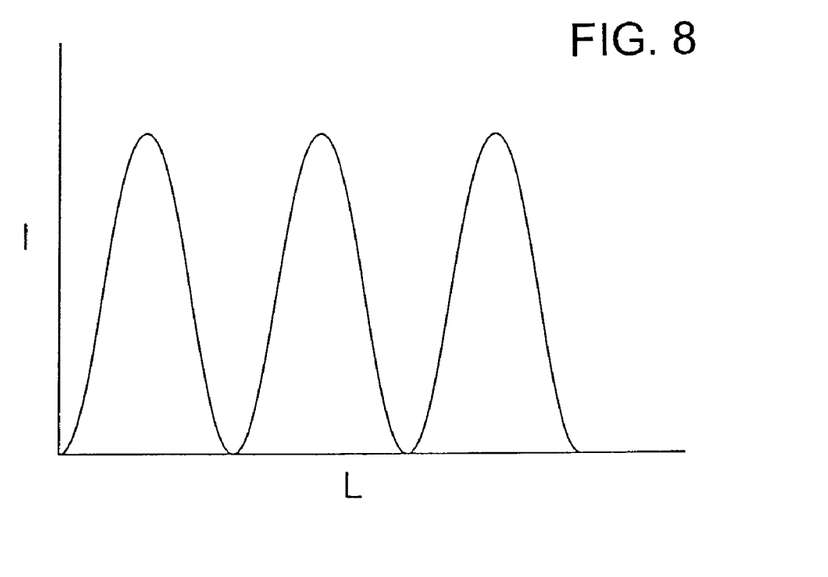
FIG. 8 shows an illumination distribution for explaining the principle of the present invention.
Figure 9:
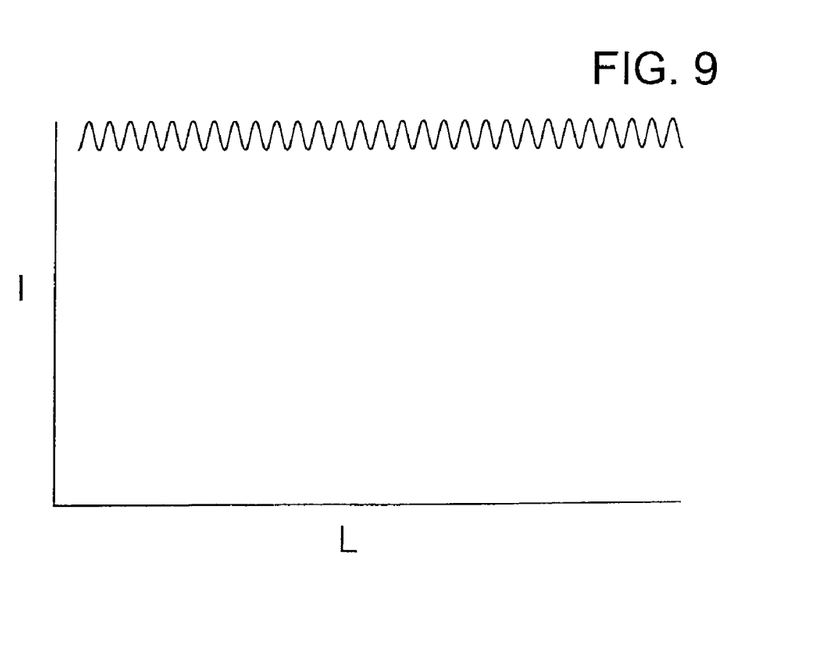
FIG. 9 shows an illumination distribution for explaining the principle of the present invention.

If the laser light emitted from the laser light source, i.e., coherent light, is concentrated onto the particle to be measured, the standing wave of the laser light forms an illumination distribution on the particle in which the light intensity (illuminance) I apparently changes with respect to relative position L, as shown in FIG. 8, that is, the light intensity defines regular illuminance fringes with high and low illuminance. On the other hand, if partial coherent light with reduced coherence is concentrated onto the particle as in the invention, the standing wave of the partial coherent light forms an illumination distribution which defines regular illuminance fringes with high and low illuminance as shown in FIG. 9. In FIGS. 8 and 9, the relative position L is plotted in abscissa and a relative illuminance I is plotted in ordinate. In FIG. 9, the amplitude of the illuminance is smaller than in FIG. 8, and the intervals of the fringes are smaller than in FIG. 8. In addition, as shown in FIG. 9, the illuminance I is composed of an constant offset component and a small fluctuation component.

According to the present invention, since the dark-field illumination with light having the standing wave shown in FIG. 9 is applied to the particle to be measured, the constant offset component does not contribute to scattering, and therefore, is not detected by the photoreceptive element.

It is generally considered that a particle scatters light when such luminance fringes exist on the surface of the particle. On the basis of this consideration, the generation of the luminance fringes is schematically illustrated in FIGS. 10(a) to 10(c) and FIGS. 11(a) to 11(b) for the case where the luminance fringes have large intervals and for the case where the luminance fringes have small intervals, respectively. In the figures, one of the luminance fringes is represented by one circle formed of a dotted line. Actually, the luminance fringes are formed all over the surface of a particle, but for simplicity of explanation, a row of circles of dotted lines is drawn on the surface of the particle in each of the figures.

Figure 10:
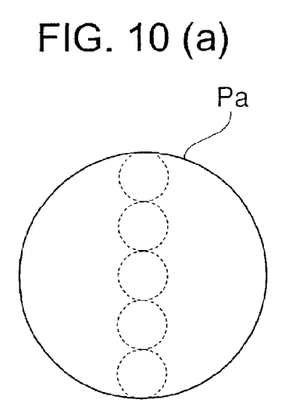

Referring to FIGS. 10(a) to 10(c), if the circles of dotted lines are large, five or four circles are formed on particles Pa, Pb and Pc having different sizes. Thus the particle Pb having a medium size cannot have 4.5 circles thereon. To sum up, in the case of large circles, the circles do not exist all over the surface of the particle Pb, and thus, the number of circles of dotted lines able to exist on the surface of one particle cannot help being a discrete value with respect to the surface area of the particle. This means that the scattered light intensity varies abruptly with respect to the size of the particles.

Figure 11:
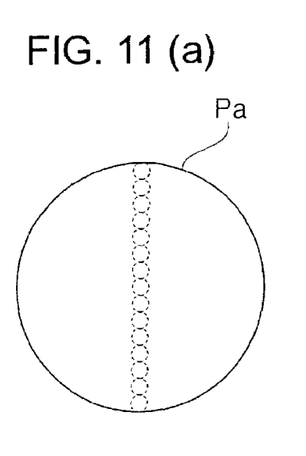

On the other hand, referring to FIGS. 11(a), 11(b) and 11(c), if the circles of dotted lines are small, a discrete degree is small for particles Pa, Pb and Pc having different sizes. That is, since circles of dotted lines can exist all over the surface of a particle, the scattered light intensity increases monotonically with the increase of the surface area of the particle, and also the particle surface area—scattered light intensity relationship can be regarded approximately as a continuous function.

Here, the particle surface area is a quadratic function of the particle diameter. Suppose that the particle diameter is X, the scattered light intensity Y is represented by $Y=aX^2+bX+c$. If a is small, Y forms a gentle parabola, and the relationship between Y and the particle size X is approximate to a linear function within a limited range of the particle size. Thus, in either case, the particle size is calculated as a monotone increasing function of the scattered light intensity in the present invention.

As the laser light source, may be used an Ar laser, a LD excited YAG+KTP laser and a semiconductor laser that are capable of emitting continuous or pulsed laser light.

As the coherence reducing element, may be used a variety of devices capable of reducing the coherence of the laser light without variations in the light intensity.

The coherence reducing element may be composed of either or both of an optical element for reducing temporal coherence and an optical element for reducing spatial coherence.

The optical element for reducing the temporal coherence may be a self-phase-modulation optical fiber, and the optical element for reducing the spatial coherence may be a kaleidoscope.

The optical element for reducing the temporal coherence may be constructed of an optical phase modulating element for broadening spectral bandwidth of light.

The optical phase modulating element in this case may be a microwave resonator with an electric-optic crystal (also referred to as a nonlinear crystal) such as a $LiNbO_3$, $LiTaO_3$, $TeO_2$ or the like arranged therein. As the optical phase modulating element, may be used Bulk Electro-Optic Modulator 4841 of NEW FOCUS, INC, for example.

Regarding how to use the optical phase modulating element, the laser light is passed through the electric-optic crystal, and a microwave is inputted to the microwave resonator from an external drive means. Thereby the spectral bandwidth of the laser light passing through the electric-optic crystal is broadened and the temporal coherence is reduced.

Thus, the optical phase modulating element can be formed of the electric-optic crystal.

Resonance by the microwave resonator can create a large electric field with a small input power. By arranging the crystal in a direction in which the crystal exhibits its electric-optical effect effectively and in the direction of the created electric field, the phase of a light cycle can be modulated efficiently. Here the light cycle means the wavelength of light. For example, in the case of light of 0.532 $\mu$m wavelength, the light corresponds to light of 563 T(tera-)Hz frequency since the velocity of light is $3 \times 10^8$ m/sec.

The coherence reducing element of the present invention may also be constructed of an optical fiber of single mode which reduces the temporal coherence.

Further the coherence reducing element may be constructed of an optical fiber and a wavefront converting element which render the spatial transmission of light and reduce the spatial coherence random.

The optical fiber in this case may preferably be an optical fiber of single mode which transmits laser light in single mode with respect to the wavelength of the laser light used. With use of the single-mode optical fiber, variations in two-dimensional light intensity distribution of input pulsed light are reduced and the light energy density is increased in a transmitting core, so that self-converging effect and self-phase-modulating effect are created. Thus it is possible to reduce not only the spatial coherence but also the temporal coherence.

The wavefront converting element may be used a seamless pipe of stainless steel whose internal surface is optically polished, a glass cylinder whose end surfaces and circumferential surface are optically polished and whose external circumferential surface further has aluminum deposition for reflecting light, or an multi-mode optical fiber of large diameter.

The wavefront converting element is so selected that a ripple in the light intensity distribution is below the resolving power of the optical system after the laser light is concentrated by the condenser lens. To sum up, the ripple does not affect the detection data of the photoreceptive element.

Since the cycle of the ripple is changed depending upon characteristics of a pulsed laser light source used, a Kalher illumination system may preferably be used for an optical illumination system including the condenser lens of a laser illumination system.

In the case where a multi-mode optical fiber is used as the wavefront converting element, the two-dimensional light intensity distribution can be stabilized more by linearly fixing the multi-mode optical fiber.

In the case where both the optical fiber and the wavefront converting element are used for the coherence reducing element, the laser light is set to be incident on the optical fiber first and then the light emitted from the optical fiber is set to be incident directly on the wavefront converting element.

In the present invention, the coherent reducing element may be constructed of the optical phase modulating element which broadens the spectral bandwidth of light to reduce the temporal coherence, and the multi-mode optical fiber and the wavefront converting element which render the spatial transmission of light random to reduce the spatial coherence.

In this case, the coherence reducing element may preferably be the optical phase modulating element, the multi-mode optical fiber and the wavefront converting element arranged in this order in the traveling direction of light.

In the present invention, the ring light forming section for converting the light emitted from the coherent reducing element into ring light may be composed of a conical external reflection mirror whose vertex is opposed to the coherence reducing element and which radially reflects the light emitted from the coherent reducing element, and a conical internal reflection mirror which surrounds the conical external reflection mirror and forms ring light from the light reflected by the conical external reflection mirror.

As the photoreceptive element, may be used a photodiode, a phototransistor, a photomultiplier tube, CCD or the like.

The calculating section is required to have the function of calculating the particle size using the monotone increasing function, and may be constructed of a microcomputer with a CPU, a ROM, a RAM and like integrated therein.

The apparatus of the present invention may further be provided with a nozzle for discharging a liquid containing the particle to be measured, and the object lens may receive light from around the tip of the nozzle. Also the apparatus may further be provided with a cell whose wall has a transparent portion, the nozzle may be inserted in the cell to oppose the transparent portion, and the object lens, located outside the cell, may receive scattered light from the particle to be measured through the transparent portion.

In another aspect, the present invention provides a method and apparatus for measuring particle size wherein the coherence of laser light emitted from a laser light source is reduced; dark-field illumination with the laser light whose coherence is reduced is applied to a particle to be measured; the intensity of scattered light from the illuminated particle is measured; and a value proportional to the intensity of the scattered light is calculated as a size of the particle.

The invention is now described in detail with reference to an example as shown in the drawings. However, the example should not be construed to limit the scope of the invention.

Figure 1:
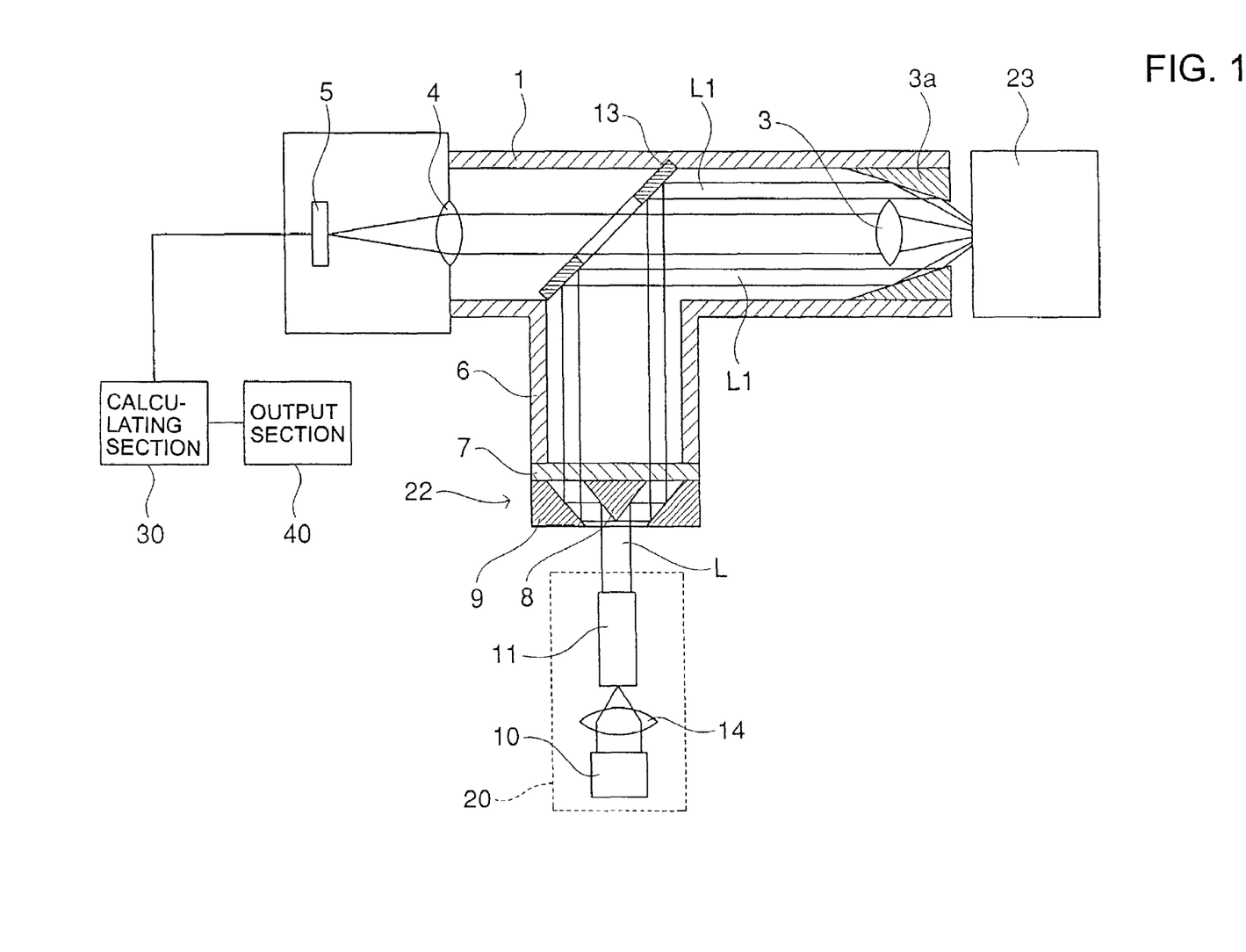
FIG. 1 is a schematic view illustrating the construction of an example in accordance with the present invention.

FIG. 1 is a schematic view illustrating the construction of an apparatus for measuring a particle size in accordance with the present invention.

As shown in FIG. 1, an object lens 3 and a conical internal reflection mirror 3a surrounding the object lens 3 are provided near a cell 23 at an end of a main lens-barrel 1, and a condenser lens 4 and a photoreceptor (e.g., a photodiode) 5 are provided at the other end.

Further, a converter 22 is fixed at a lower end of an illumination lens-barrel 6. The converter 22 has a light-transmissive plate 7, a conical external reflection mirror 8 mounted at the center of the lower surface of the plate 7 and a conical internal reflection mirror 9 mounted at the periphery of the lower surface. Outside the illumination lens-barrel 6, is provided a light source unit 20 including a laser light source 10, an inlet lens 14 and a coherence reducer 11. An annular plane mirror 13 is provided in the center of the main lens-barrel 1.

Figure 2:
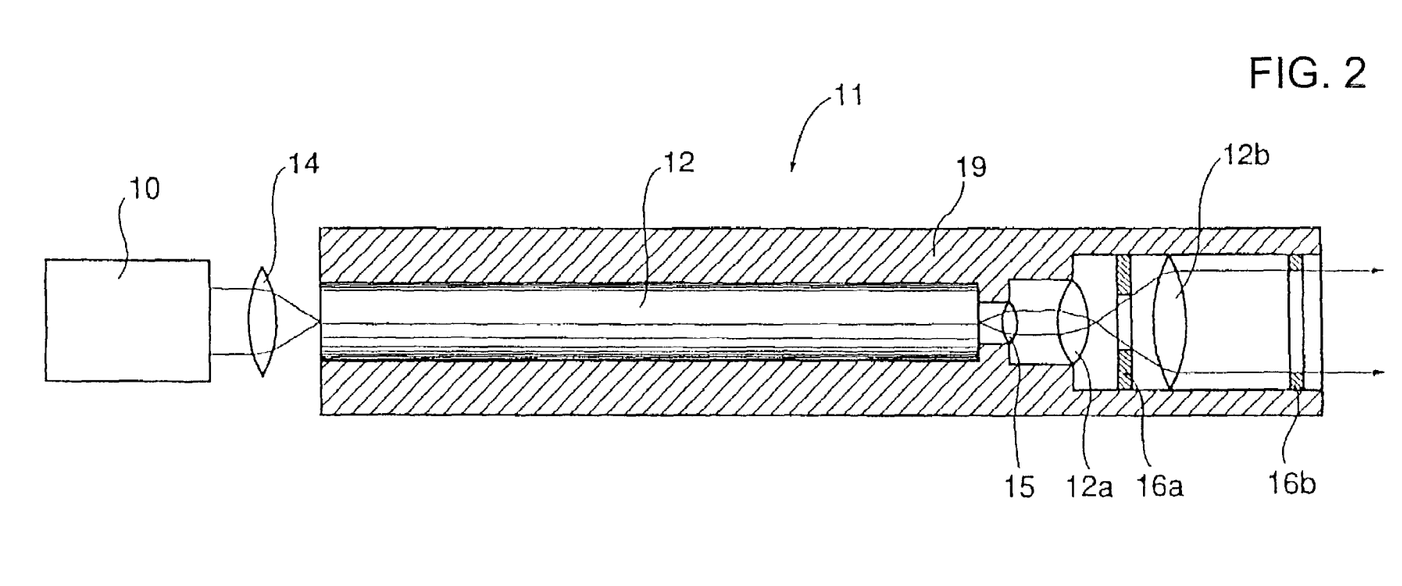
FIG. 2 is a detailed sectional view of a major part of FIG. 1.

FIG. 2 is a detailed sectional view of the coherence reducer 11 shown in FIG. 1.

As shown in FIG. 2, the coherence reducer 11 includes a support member 19 and an optical fiber 12 within the support member 19. Light coming out of the light fiber 12 is emitted outward through a collimator lens 15 and beam expander lenses 12a and 12b. Reference numerals 16a and 16b each denote field irises (iris diaphragms) for reducing the diameter of a ray of light.

In this example, a semiconductor laser (7300 produced by Spectra-Physics Co., Ltd.) of 532 nm wavelength is used as the laser light source 10, and Kaleidoscope (large-diameter multi-mode optical fiber MKH-08 produced by Sumitomo Electric Industries) is used as the optical fiber 12 of the coherence reducer 11. The light-transmissive plate 7 is formed of a plate of PMMA of 3 mm thickness whose both faces are finished to have almost the same roughness as the wavelength of the laser light.

Figure 3:
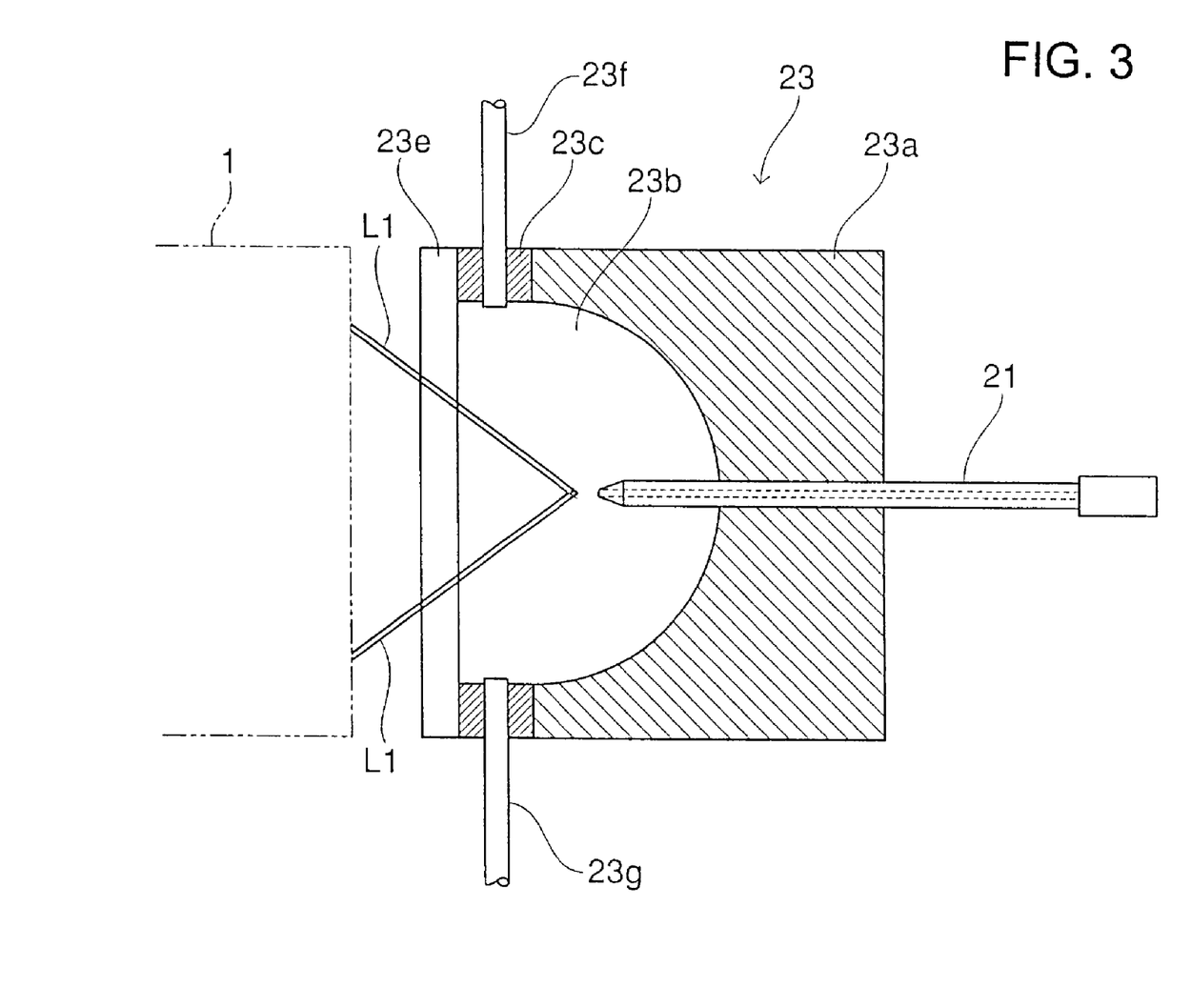
FIG. 3 is a detailed sectional view of a major part of FIG. 1.

FIG. 3 is a detailed sectional view of the cell 23. The cell 23 has a body 23a having a hemispherical hollow 23b. A transparent glass plate 23e is attached to the opening of the hollow 23b with intervention of a ring spacer 23c. Thereby the hollow 23b is closed tightly.

The body 23a is formed of a chemical-resistant stainless steel (SUS316). A nozzle 21 is formed of the stainless steel (SUS316) and is provided to pass through the body 23a so that the tip of the nozzle 21 is situated in the center of the hollow 23b. Two drainage tubes 23f, 23g are provided through the ring spacer 23c.

In this construction, when a particle-containing liquid (liquid containing a particle to be measured) is discharged from the tip of the nozzle 21 into the cell 23, the flow rate of the liquid is adjusted so that for the liquid forms a laminar flow in the cell 23, taking into consideration the inner diameter of the nozzle 1 and the profile of an inside wall of the nozzle 1.

Next, as shown in FIG. 1, a ray of light emitted from the laser light source 10 passes through the inlet lens 14 and reaches the coherence reducer 11, where its coherence is reduced and the light intensity distribution is flattened. A ray of light L emitted from the coherence reducer 11 is incident onto the conical external reflection mirror 8 and is reflected thereby 360° radially.

The radially reflected ray of light L is then reflected by the conical internal reflection mirror 9 in the vertical direction to be converted into ring light. The ray of light L converted into the ring light passes through the light-transmissive plate 7, then is reflected by the annular plate mirror 13 toward the object lens 3, and further is reflected by the conical internal reflection mirror 3a to be incident onto the cell 23 from all directions of 360° around the object lens 3.

Figure 4:
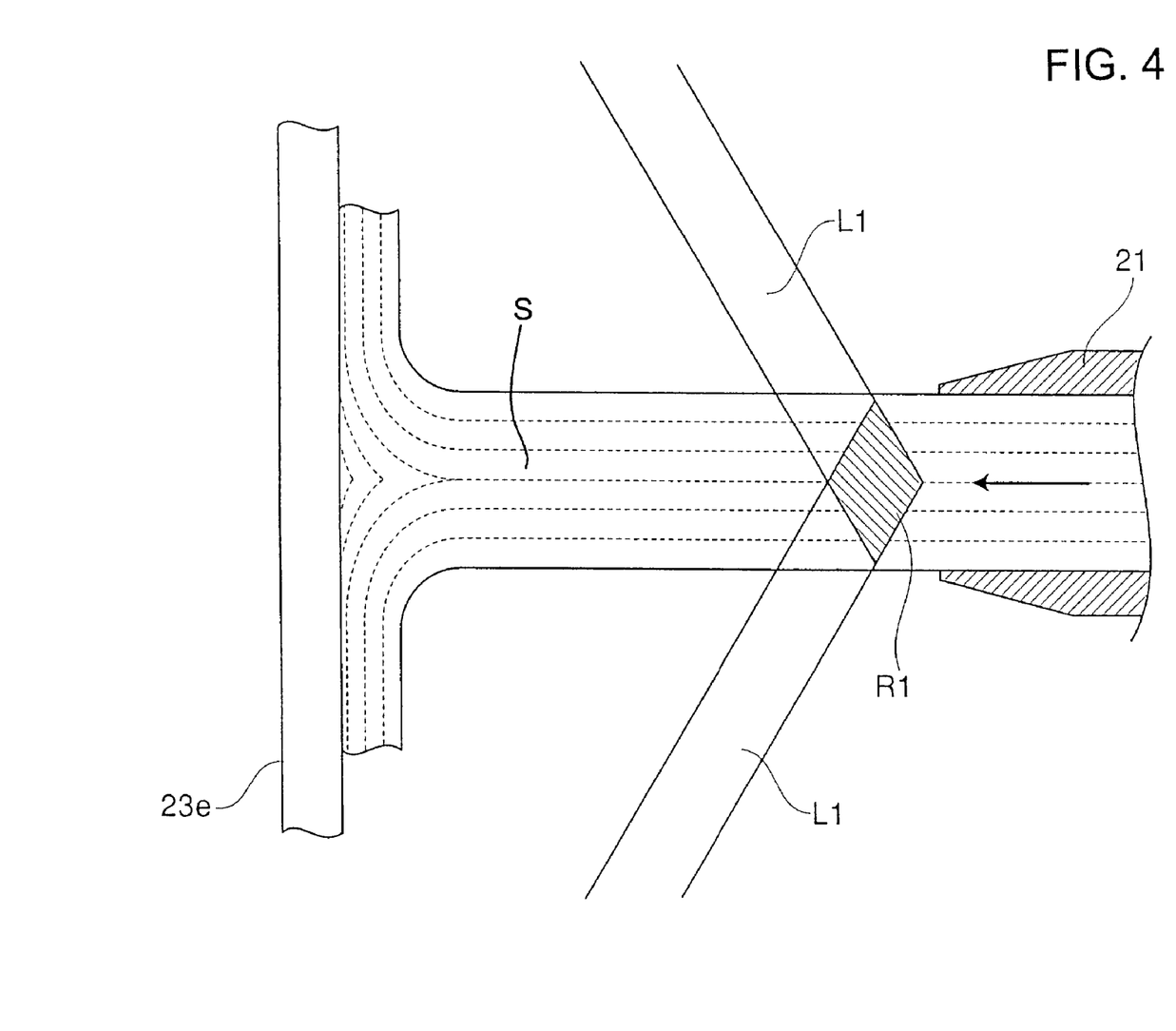
FIG. 4 is an enlarged view of a major part of FIG. 3.

FIG. 4 is an enlarged view of a major part of the cell 23, showing the state of the particle-containing liquid S being discharged from the tip of the nozzle 21 toward the transparent glass plate 23e. At the tip of the nozzle 21, a dark-field illumination region R1 is formed by the ray of light L1 in the laminar flow of the discharged particle-containing liquid S.

Figure 5:
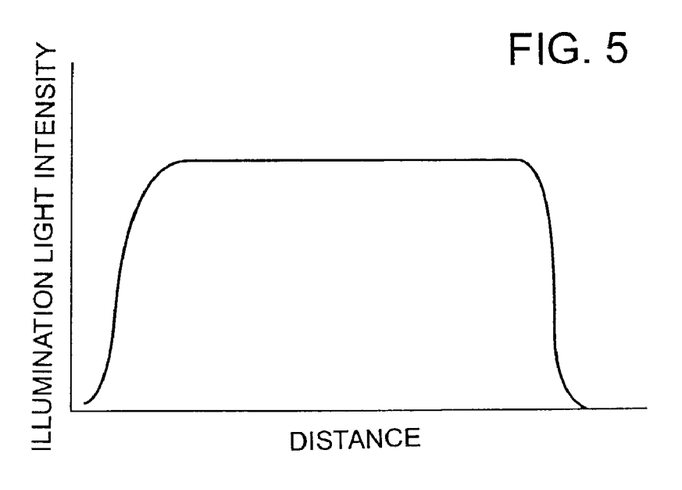
FIG. 5 is a graph showing intensity distribution of illumination light within dark-field illumination range.

In this case, by rendering the intensity distribution of the ray of light L1 uniform, a uniform illumination light intensity can be obtained in the region R1 with respect to distances in the direction perpendicular to the flow, as shown in FIG. 5. This reduces variations in the detected scattered light intensity which might occur owing to different positions of passing particles in the direction perpendicular to the flow.

As described above, the coherence reducer 11 reduces the coherence of the laser light from the laser light source 10 so sufficiently that the light intensity distribution is flattened. The light-transmissive plate 7 further reduces the spatial coherence since the plate 7 changes the optical phase of the laser light by almost the same roughness of its surface as the wavelength of the laser light.

On the other hand, scattered light from a particle illuminated by the ray of light L1 in the dark-field illumination region R1 is received by the object lens 3 shown in FIG. 1 and then focused on the photoreceptor 5 by the condenser lens 4. A calculating section 30 shown in FIG. 1 calculates the particle size from the intensity of the scattered light detected by the photoreceptor 5 and outputs the calculation results on an output section 40.

Figure 6:
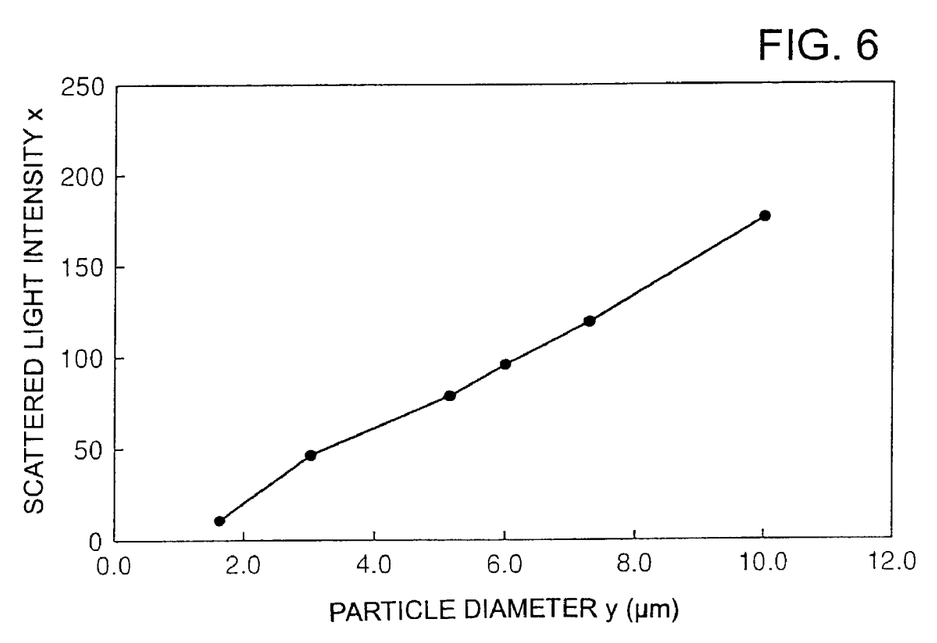
FIG. 6 is a graph showing a relationship between the particle size and the intensity of scattered light obtained in an example.

FIG. 6 is a graph showing a relationship between the particle diameter y and the intensity x of scattered light actually determined by the apparatus for measuring the particle size of this example. Latex particles of 1.5 to 10 $\mu$m diameter were used as particles to be measured. FIG. 6 shows that the particle diameter is in a relationship substantially proportional to the scattered light intensity x.

That is, it has been found that the particle diameter y is represented by a linear function of the scattered light intensity x as follows:

$$y = ax + b \quad (a \text{ and } b \text{ are constants}) \quad (1)$$

Accordingly, the calculating section 30 can easily calculate the particle diameter using the formula (1).

Figure 7:
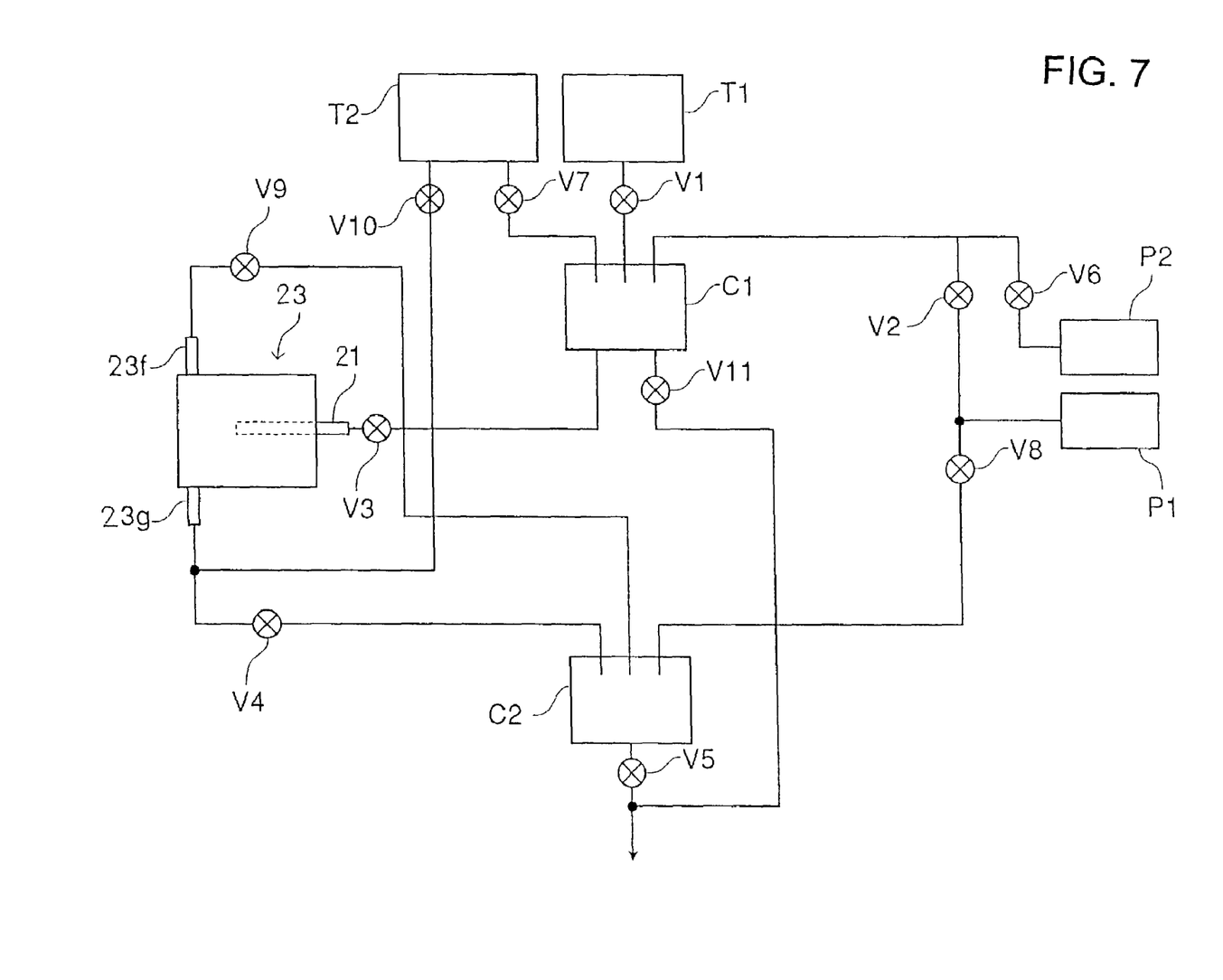
FIG. 7 is a block diagram showing a fluid system of an example.

Here, further explanation is given of the construction and operation of a fluid system for supplying and discharging the particle-containing liquid to and from the cell 23 with reference to FIG. 7.

In measurement steps, valves V1 and V2 are opened first to supply the liquid containing particles to be measured from a sample solution tank T1 into a sample chamber C1 by negative pressure of a negative pressure pump P1. When the supply of the particle-containing liquid is completed, the valves V1 and V2 are closed.

Then, when valves V3, V4, V5 and V6 are opened, the particle-containing liquid is discharged from the sample chamber C1 into the cell 23 through the valve V3 and the nozzle 1 by positive pressure of a positive pressure pump P2. The particle-containing liquid in the cell 23 is discharged into a waste liquid chamber C2 through the drainage tube 23g and the valve V4 and further discharged to outside through the valve 5. During this process, the scattered light intensity is measured as described above. When this process is finished, the valves V3, V4, V5 and V6 are closed.

Next, a washing process for a flow path is performed. Valves V7, V3, V4 and V8 are opened to let a washing liquid flow from a washing liquid tank T2 through the valve V7, the sample chamber C1, the valve V3, the nozzle 1, the cell 23, the valve V4 and the waste liquid chamber C2 by negative pressure of the negative pressure pump P1 to wash the flow path. When this washing process is finished, the valves V7, V3, V4 and V8 are closed.

Next, a washing process for the cell 23 is performed. Valves V10, V9 and V8 are opened to supply the washing liquid flow from the washing liquid tank T2 to the cell 23 through the valve V10 and the drainage tube 23g by negative pressure of the negative pressure pump P1. The washing liquid is then discharged to the waste liquid chamber C2 through the valve V9. When this washing process is finished, the valves V10, V9 and V8 are closed.

Next, a washing process for the sample chamber C1 is performed.

First, valves V7 and V2 are opened to supply the washing liquid from the washing liquid tank T2 to the sample chamber C1 through the valve V7 by negative pressure of the negative pressure pump P1.

Next, the valves V7 and V2 are closed and the valves V6 and V11 are opened to discharge the washing liquid from the sample chamber C1 through the valve V11 by the positive pressure of the positive pressure pump P2. After the supply and discharge of the washing liquid to and from the sample chamber C1 is repeated a plurality of times, the washing process for the sample chamber C1 is finished.

According to the present invention, by applying the dark-field illumination with the laser light whose coherence is reduced to the particle to be measured, the intensity of the scattered light from the particle is represented by a monotone increasing function of the particle size. Therefore, the particle size can be effectively determined by a simple apparatus and simple data processing.

What is claimed is:

1. A particle size measuring apparatus comprising:
    a laser light source;
    a coherence reducing element for receiving laser light emitted by the laser light source, reducing coherence of the laser light and emitting the laser light whose coherence is reduced;
    a ring light forming section for converting the light emitted by the coherence reducing element into ring light;
    an internal reflection mirror for concentrating the ring light on a particle to be measured and illuminating the particle;
    an object lens for receiving scattered light from the illuminated particle inside the ring light;
    a photoreceptive element for receiving the scattered light through the object lens; and
    a calculating section for calculating a size of the particle from an intensity of the scattered light obtained by the photoreceptive element by using a monotone increasing function.

2. A particle size measuring apparatus according to claim 1, wherein the ring light forming section comprises a conical external reflection mirror whose vertex is opposed to the coherence reducing element and which radially reflects the light emitted from the coherent reducing element and a conical internal reflection mirror which surrounds the conical external reflection mirror and receives the light reflected by the conical external reflection mirror to form the ring light.

3. A particle size measuring apparatus according to claim 1, wherein the coherent reducing element comprises an optical fiber.

4. A particle size measuring apparatus according to claim 1, wherein the monotone increasing function is a linear function.

5. A particle size measuring apparatus according to claim 1 further comprising a nozzle for discharging liquid, wherein the particle to be measured are contained in the liquid, and the object lens receives the scattered light from a direction of a tip of the nozzle.

6. A particle size measuring apparatus according to claim 5 further comprising a hollow cell whose wall has a transparent portion, wherein the nozzle is inserted in the cell so that the tip of the nozzle is opposed to the transparent portion, and the object lens is situated outside the hollow cell to receive the scattered light from the particle through the transparent portion.

* * * * *